US012699093B2

(12) United States Patent
Anik et al.

(10) Patent No.: US 12,699,093 B2
(45) Date of Patent: Aug. 4, 2026

(54) BIOSENSOR AND METHOD FOR DETERMINATION OF VIRUSES IN CORONAVIRUS FAMILY

(71) Applicant: MUGLA SITKI KOCMAN UNIVERSITESI, Mugla (TR)

(72) Inventors: Ulku Anik, Mugla (TR); Yudum Tepeli Buyuksunetci, Mugla (TR)

(73) Assignee: MUGLA SITKI KOCMAN UNIVERSITESI, Mugla (TR)

( * ) Notice: Subject to any disclaimer, the term of this patent is extended or adjusted under 35 U.S.C. 154(b) by 548 days.

(21) Appl. No.: 18/265,974

(22) PCT Filed: Nov. 16, 2021

(86) PCT No.: PCT/TR2021/051214
§ 371 (c)(1),
(2) Date: Jun. 8, 2023

(87) PCT Pub. No.: WO2022/150024
PCT Pub. Date: Jul. 14, 2022

(65) Prior Publication Data
US 2024/0094206 A1     Mar. 21, 2024

(30) Foreign Application Priority Data
Jan. 11, 2021     (TR) ................................. 2021/00352

(51) Int. Cl.
| | |
|---|---|
| *G01N 33/52* | (2006.01) |
| *G01N 33/53* | (2006.01) |
| *G01N 33/543* | (2006.01) |
| *G01N 33/569* | (2006.01) |

(52) U.S. Cl.
CPC . *G01N 33/56983* (2013.01); *G01N 33/54326* (2013.01); *G01N 2333/165* (2013.01); *G01N 2333/70596* (2013.01); *G01N 2458/30* (2013.01); *G01N 2469/10* (2013.01)

(58) Field of Classification Search
None
See application file for complete search history.

(56) References Cited

U.S. PATENT DOCUMENTS

| | | | |
|---|---|---|---|
| 2021/0298649 A1* | 9/2021 | Essalik | ................ A61B 5/1477 |
| 2023/0137756 A1* | 5/2023 | Kulp | .............. C12Y 304/14005 |
| | | | 424/134.1 |
| 2023/0228752 A1* | 7/2023 | Hülsmann | .......... G01N 21/6428 |
| | | | 435/5 |

OTHER PUBLICATIONS

Büyüksünetçi et al., Analyst, 2022, published Nov. 8, 2021, 147:130-138 (Year: 2022).*
Xiaoyan Zhang, et al., Electrical probing of COVID-19 spike protein receptor binding domain via a graphene field-effect transistor, 2020, pp. 1-20.
Shimaa Eissa, et al., Development of a Low-Cost Cotton-Tipped Electrochemical Immunosensor for the Detection of SARS-CoV 2, Analytical Chemistry, 2021, pp. 1826-1833, vol. 93.
Bartolomeo Della Ventura, et al., Colorimetric Test for Fast Detection of SARS-CoV 2 in Nasal and Throat Swabs, ACS Sensors, 2020, pp. 3043-3048, vol. 5.
Li Yanbin, Section 2.3 Biosensors, CIGR Handbook of Agricultural Engineering vol. VI Information Technology, 2006, pp. 60-102, vol. VI.
Gabriele Wagner, et al., Food Biosensor Analysis, Trends in Food Science & Technology, 1995, pp. 250-251, vol. 6.

* cited by examiner

*Primary Examiner* — Stacy B Chen
(74) *Attorney, Agent, or Firm* — Bayramoglu Law Offices LLC

(57) ABSTRACT

A method and a biosensor for determination of the presence of corona-virus are provided. The method includes qualitative or quantitative measurement of probable corona-virus presence by means of colorimetric and/or electrochemical transducer methods as a result of interaction of S-protein in patient samples by means of a biosensor including ACE2, DPP4 and CD147 bio-receptors as bio-receptor.

10 Claims, 2 Drawing Sheets

BIOSENSOR AND METHOD FOR DETERMINATION OF VIRUSES IN CORONAVIRUS FAMILY

CROSS REFERENCE TO THE RELATED APPLICATIONS

This application is the national phase entry of International Application No. PCT/TR2021/051214, filed Nov. 16, 2021, which is based upon and claims priority to Turkish Patent Application No. 2021/00352, filed on Jan. 11, 2021, the entire contents of which are incorporated herein by reference.

TECHNICAL FIELD

The present invention relates to a biosensor developed by referencing infection mechanisms of corona-virus and other similar diseases and which can be used in diagnosis of mentioned diseases.

The present invention relates to a diagnosis method where a patient can test himself/herself and can learn the test result in short times by means of biosensor developed by referencing infection mechanisms of corona-virus and other similar diseases.

BACKGROUND

Corona-viruses are a big virus family which can lead to diseases in animals or in humans. It is known that a number of corona-viruses lead to respiratory path infections like common cold, Middle East Respiratory Syndrome (MERS) and Severe Acute Respiratory Syndrome (SARS). It is very important that said diseases are diagnosed early in order to be able to start the treatment early and in order to be able to prevent infecting speed.

PCR (Polymerase Chain Reaction) is defined as a mutual name given to reactions applied for enzymatic reproduction of a unique region found in DNA and provided between two segments with known arrays. PCR is known as a diagnostic test and can show the RNA which belongs to the virus.

PCR test, which is also used for different diseases, can detect even very small number of microbes in the body. PCR test can also be called molecular diagnostic test. The test can determine the presence of virus in the body and the antibodies produced by the body as a response to the infection. PCR analyses are among time-taking methods which do not have high precision. Moreover, such methods must be realized by specialists and include expensive instrumentations.

A Biosensor basically comprises a bio-recognition element and a transducer and is used in the detection of biological and chemical analytes. Biosensors can select and diagnose target analytes via transducers like electrochemical, optical, piezoelectric, thermal and magnetic devices and via bio-recognition elements including enzymes, antibodies, nucleic acid examinations, cells, tissues and organelles. Biosensors can be used on-line and/or real-time manner with low cost and rapid manner and with high precision in the operation field of agricultural production, food processing, environmental tracking activities, plants, animals, foods, soil, air and water, pesticides, antibiotics, pathogens, toxins, proteins, nutrilites, bad smells, microbes and more, by coming together with new technologies like molecular biology, micro-fluids and nano-materials. [P. Demircioğlu and I. Börekçi]

Bio-recognition element is in close contact with a device called transducer. In general, biosensor is a device which can transform biological, chemical or biochemical signal into measurable and processable electrical signal and comprising biological sensing material joined with chemical or physical transducer. [Wangner, G, and G. G. Guibault, eds. 1994. Food Biosensor Analysis. New York, NY: Marcel De kker]

Colorimetric biosensors operate frequently by sensing bio-molecules and metal ions. Since their response signals are visible, the results are directly seen by the eye. In colorimetric biosensors, special equipment is not needed for obtaining result, and by means of this, the cost of biosensors and thus the costs of tests can be substantially reduced.

In electrochemical biosensors, transducer is generally formed by an electrode. There are different types of electrochemical biosensors. In potentiometric biosensors which are one of these, the potential change which occurs after bio-reaction is tracked. In voltammetric biosensors, potential is scanned in a specific range, and obtained current values that are occurred due to a bio-electrochemical reaction are measured. In recent years, bio-sensors that are based on electrochemical impedance spectroscopy (EIS) have been developed where, the contribution of each molecule, that is connected to the electrode surface, on electron resistance is tracked.

It is seen that abovementioned biosensors are used in diagnosis or treatment of various diseases. It is considered that biosensors, which have different characteristics and moreover which are obtained in various forms, can also be used in early diagnosis of corona-viruses. Practicality, speed, selectivity and low cost provided by these biosensors are increasing their usage potentials as diagnostic kits.

Corona-viruses are viruses which necessitate early diagnosis. In case of any infection, the individual must rapidly isolate himself/herself and thanks to this isolation, the virus must be prevented from infecting to other healthy individuals. Therefore, in the related technical field, fast, efficient and easily accessible diagnostic devices and methods are needed As a result, because of the abovementioned problems and because the present methods need specialists and expensive instruments; developments, which will eliminate these disadvantages, must be made in the related technical field.

SUMMARY

The present invention relates to a biosensor and measurement method which can be used in corona-virus diagnosis in individuals, for eliminating the abovementioned disadvantages and for bringing new advantages to the related technical field.

An object of the present invention is to provide a rapid, precise and unique method and biosensor for diagnosis and measurement of corona-virus.

An object of the present invention is to provide a method and biosensor which do not need any specialist where patient can realize corona-virus test by himself/herself.

An object of the present invention is to provide a method and biosensor having low cost and which are easy to use and which are portable for the determination and measurement of corona-virus.

An object of the present invention is to provide a method and biosensor which are easier to prepare when compared with other methods and biosensors in the related technical field in order to be obtained for the determination and measurement of corona-virus.

REFERENCE NUMBERS

Figure 1:
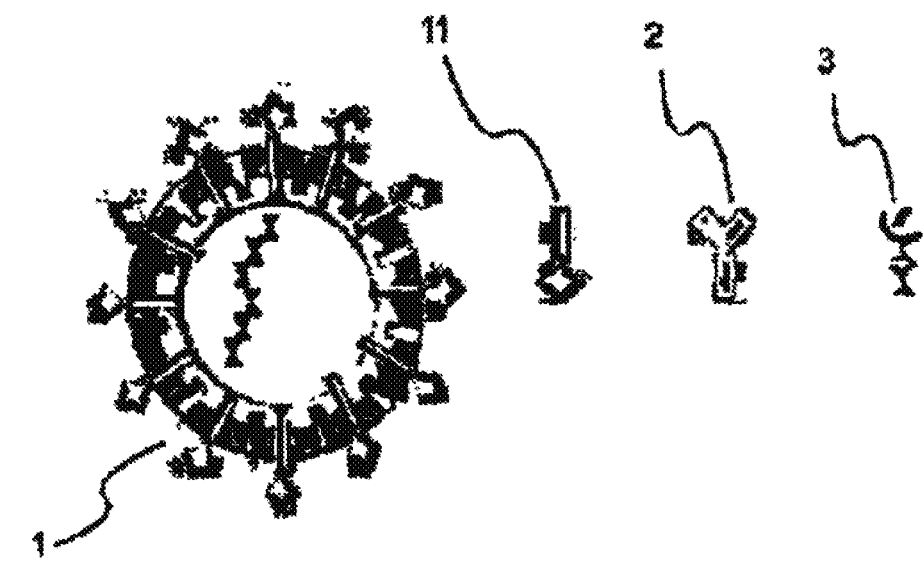
In FIG. 1, the schematic representations of the structure of corona-virus, bio-receptor, spike protein and human enzymes are given.

1 Corona-virus
11 Spike protein
2 Bio-receptor
3 Human enzyme
4 Electrode

DETAILED DESCRIPTION OF THE EMBODIMENTS

In this detailed description, the subject matter is a method and a biosensor for early diagnosis of corona-viruses (1) and is explained with references to examples without forming any restrictive effect only in order to make the subject more understandable. The method and the biosensor enable diagnosis of corona-virus (1) presence from the samples obtained from a viable organism. The used biosensor and method comprise very simple equipment and have structure such that the patient can test himself/herself in short times and can analyze the result of the test.

As known, biosensors comprise two main structures. These structures are at least one bio-receptor (2) which comprises biochemically active components, and at least one transducer which provides converting of the biological event into electrical signals.

The biosensor obtained in the present invention comprises protein and enzymes as bio-receptor (2). The basic principle in the invention is that the enzyme and/or protein, to be used as bio-receptor, interact(s) with corona-virus (1) and a biological event occurs as a result of this interaction and the part, to be used as transducer, senses this biological event and it is analyzed whether the person has this virus or not. In general, as the bio-receptor (2) which will provide concerned interaction, ACE2, DPP4 and CD147 enzymes are used.

The name of ACE2 enzyme in the technical field is angiotensin transformer enzyme. ACE2 enzymes are enzymes bonded to the outer surface (cell membrane) of the cells in lungs, arteries, heart, kidneys and intestines. The task of the ACE2 enzyme is to accelerate hydrolysis of vein narrowing angiotensin II hormone into angiotensin (1-7) and to reduce blood pressure. As also known in the art, the corona-viruses (1) use ACE-2 receptors as input point to the cells.

Dipeptidyl peptidase-4 (it will be shortened as DPP-4) is a member of protease family. DPP-4 is at the same time known as protein (ADBP) which binds adenosine deaminase or as T-cell activation antigen CD26. DPP-4 catalyses separation of pirolin, hydroxy-pirolin, dehydro-pirolin or alanin provided at the final place of N-terminal peptide of a protein. DPP-4 exists in two forms in blood, namely free and bonded forms.

CD147 is a member of immunoglobulin upper family and has a structure related to the assumed primitive form of the family. Since the members of immunoglobulin super family play basic roles in various immunologic phenomena, differentiation and recognition between cells in development, it is considered that basigin plays a role in recognition between the cells.

Figure 2:
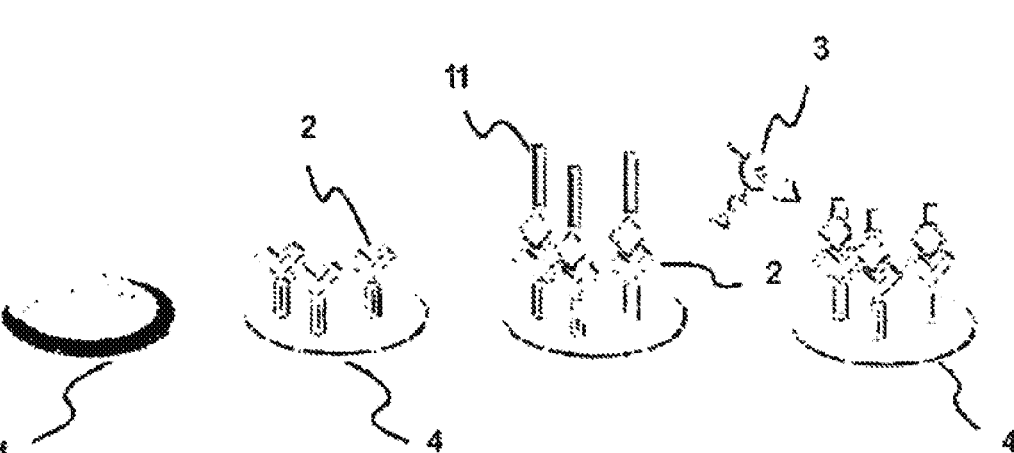
In FIG. 2, the schematic representation of the process steps of electrochemical biosensor including the interactions of bio-receptor and the corona-virus spike proteins and the placement of bio-receptors on the electrode and the biosensor including electrochemical method as the transducer and the electrode provided in the body thereof is given.

In FIG. 1, schematic representation of corona-virus (1) is given. As also seen here, the viruses in corona-virus (1) family have spike proteins (11) (will be shortened as S protein). The bio-receptors (2) provided in the biosensor mentioned in the invention are embodied to interact with said S proteins (11). The interaction of bio-receptor (2) and S protein (11) is shown in FIG. 2 in a representative manner.

The interaction of bio-receptor (2), used in the invention, and the corona-viruses (1) has been proven by means of the studies in the literature. The base of this interaction is that receptor binding domain (will be shortened as RBD) exists in S proteins (11) which exist in corona-viruses (1). The given enzymes, even if they are not completely illuminated, interact with RBD parts of S proteins (11) of corona-virus (1) and provide the biologic event which is needed for the operation of the biosensor.

The biosensor obtained in the invention comprises at least one transducer which transforms the biological event, formed as a result of enzyme-virus interaction, into the desired measurement values. In the invention, the biological event between enzyme-virus can be measured by means of two different methods. Said transducer methods are electrochemical and colorimetric methods.

The subject matter relates to inclusion of embodiments related to being able to realize quantitative or qualitative measurements in the subject of whether persons have corona-virus (1) or not in the in vitro conditions of biosensors comprising ACE2, DPP4 and CD147 enzymes which are known beforehand to be effective with corona-virus (1). Within this context, the biosensor, comprising analyte-bioreceptor (2)-transducer embodiment basically, comprises the followings:

analyte taken from the person who is suspected to be patient,
ACE2, DPP4 and CD147 enzymes as bio-receptor (2),
electrochemical or colorimetric structures as transducer.

In the invention, the analyte, where the biosensor is desired to diagnose the presence of corona-virus, can be obtained preferably from the mouth and/or nose in human body by means of swab method.

The basic embodiment of bio-receptors (2) obtained in the invention shows difference when compared with the virus in corona-virus (1) family. Accordingly, ACE2 bio-receptors are used for SARS and SARS-2, DPP-4 bio-receptors are used for MERS, and CD147 bio-receptors (2) are used for SARS-2.

The embodiment provided in the invention is essentially based on colorimetric qualitative measurement. Accordingly, the obtained colorimetric biosensor comprises a chemical component which provides color change which shall take place in the presence of corona-virus (1). Blue colored oxidizing compound is used as said chemical component. As said solution, $\gamma\text{-Fe}_2O_3$ magnetic nano-particles and 3,3',5,5'-tetramethylbenzidine solution including $H_2O_2$ are used. When the binding region of the S protein (11), which exists in corona-virus (1) body, binds to the bio-receptor (2) which exists on the healthy cell surface, thanks to the arrangement which occurs in molecules, $H_2O_2$ including blue colored oxidized form TMB solution, oxidizes the thiol in this structure and is reduced and therefore the blue color disappears. Within this context, color change (in other words, decolorization of the solution) indicates the presence of corona-virus (1) in the body of the analyte taken from the patient.

In an embodiment of the invention, the biosensor is embodied by including electrochemical transducer. In FIG. 2, the schematic representation of a biosensor including electrochemical method as transducer is given. In this embodiment, there is the electrode (4) which can realize electrochemical measurement. These bio-receptors (2) are immobilized by means of cross-binders like 1-Ethyl-3-(3-dimethylaminopropyl) carbodiimide (EDC)/N-hydroxysuccinimide (NHS) onto the electrodes (4) obtained commercially. In the analyte sample taken from the patient, in the presence of corona virus, S-protein (11) provided in the body thereof and the suitable bio-receptor (2) shall interact. As a result of this, the impedance or resistance of the electrode (4) shall increase. This differentiation shall be examined by means of EIS method. TMPRSS2 enzyme shall be added to the medium for finalizing this bonding in other words the virus presence, and this enzyme cleavages the S-protein (11), which exists on the virus, from the S2 sub-unit and this leads to further increasing of the impedance. All of these shall be examined by means of EIS method step by step. The structure where the electrochemical method shall be used as transducer in the biosensor is obtained as follows: Here, as said electrodes (4), in general, screen printed, gold or carbon-based electrodes (4) can be used. Various operation conditions are optimized by tracking the impedance change on electrode (4) surface by means of EIS. Afterwards, analytical characteristics are examined.

Independent from the realization of the measurements by means of colorimetric method or by means of electrochemical transducers, in the subject matter biosensor, the basic reaction is provided by means of reaction of the bio-receptors (2) and the corona-virus (1). The biological event here is based on binding of S-protein (11), which exists on the virus surface, to one of the pre-mentioned three bio-receptors (2) which change in accordance with the strain of corona-virus (1). The presence of such an interaction is certain; and by means of measuring of the obtained biological event, the patient can understand if he/she has corona-virus (1) without needing any specialist interpretation particularly thanks to the colorimetric system.

Determination Method by Means of Biosensor

Usage of Electrochemical Method as Transducer

The swabs, taken from the noses of the persons where corona-virus (1) determination and measurement shall be made, are taken to the electrode (4) surface for electrochemical biosensor. The occurring changes are tracked electrochemically.

In corona-virus (1) determination by means of biosensor where electrochemical method is used as transducer, the following process steps are applied;

Contacting of the analyte, taken from the patient, to the bio-receptors (2) immobilized onto the suitable working electrode (4), Occurring of interaction between the bio-receptors (2) and the S-proteins (11) of the probable corona-viruses (1) which exist in the analyte, Cleavage of the binding protein of the enzyme, which shall be added to the medium, from the specific region, Understanding by the person whether he/she is sick or not by tracking the change which occurs in the resistance or impedance of the electrode (4), as a result of the reactions which take place on the electrode (4) surface.

In the used biosensor, ACE2, DPP4 and CD147 enzymes take charge as bio-receptor. The suitable ones of these bio-receptors (2) are immobilized onto the electrode (4) surface. Here, binding is formed thanks to the S-protein (11) provided in the virus structure. For further confirming the binding, enzyme TMPRSS2 which provides cutting of S-protein (11) is added onto the electrode (4) surface.

Figure 3:
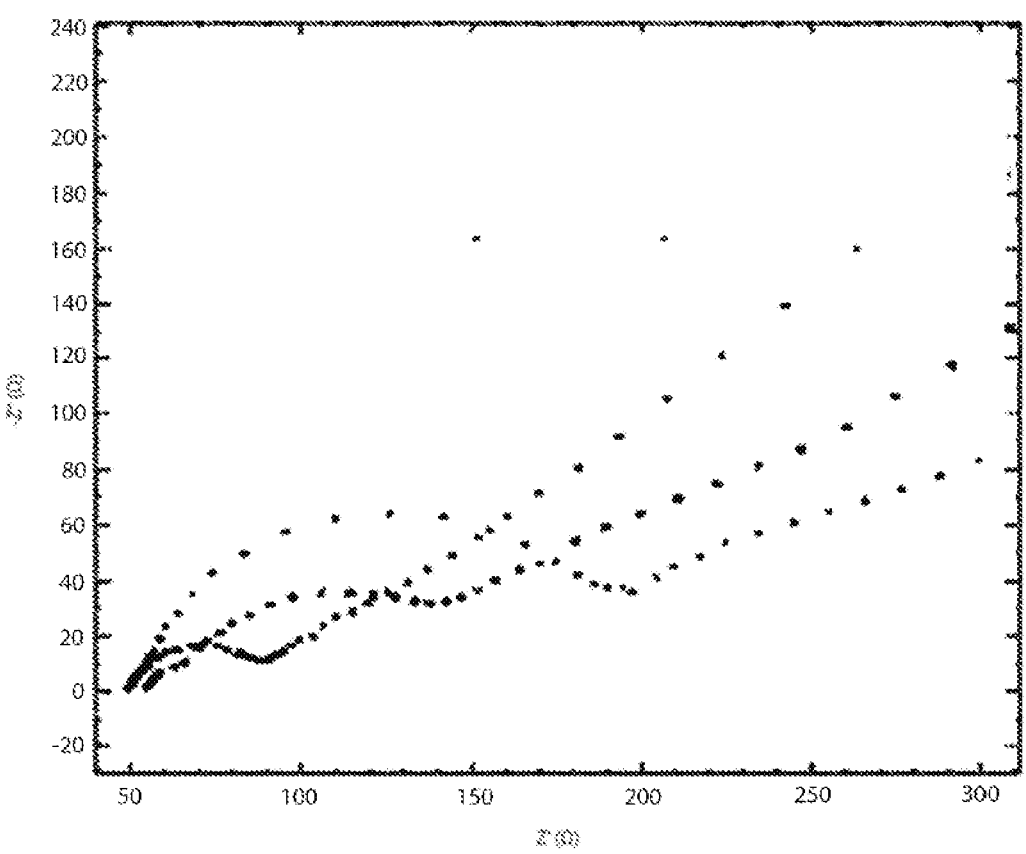
In FIG. 3, the impedance values between the analyte and the subject matter electrochemical biosensor are given.

As seen in EIS Nyquist curve which exists in FIG. 3, as a result of binding of bio-receptor (2) by means of suitable cross-binders onto the golden electrode (4), electron transfer has been prevented at some degree because of a layer which occurs on the electrode (4) surface. This will cause an increment of the resistance onto the electrode surface. Moreover, a second layer is further formed on the electrode (4) surface by means of receptor-S protein (11) interaction which takes place as a result of incubation of bio-receptor (2) with S-protein (11), and resistance against electron passage is formed. Finally, the highest resistance is formed as a result of interaction of TMPRSS2 enzyme in order to cleavage S-protein (11). By means of this, by mimicking the infection steps of the virus, a diagnostic method has been developed.

Usage of Colorimetric Method as Transducer

The swab, taken from the noses of the persons where corona-virus (1) determination and measurement shall be made, is taken to eppendorf tubes where color changing chemical components are provided. The occurring changes are examined by means of qualitative observation.

In corona-virus (1) determination by means of biosensor where colorimetric method is used as transducer, the following process steps are applied;

firstly adding color forming and oxidizing reagent solution into the eppendorf tube and afterwards obtaining blue colored reagent-bio-receptor (2) solution, adding the analyte obtained from the patient into the above reagent solution and mixing and disappearance of blue color as a result.

In this method, blue colored oxidizing compound is used. As said reagent solution, $\gamma$-$Fe_2O_3$ magnetic nano-particles and 3,3',5,5'-tetramethylbenzidine solution including $H_2O_2$ are used. When the binding region of S-protein (11) provided in the body of corona-virus (1) is bonded to the bio-receptor (2) provided on the healthy cell surface, thanks to the arrangement which occurs in the molecules, blue colored oxidized TMB including $H_2O_2$ solution oxidizes the thiol in this structure to disulfide bonds, while it is reduced, and therefore, the blue color disappears. Within this context, color change in other words, decolorization of the solution, indicates the presence of corona-virus (1) in the body of the analyte taken from the patient.

When colorless TMB solution, which includes $H_2O_2$, comes together with $\gamma$-$Fe_2O_3$ magnetic nanoparticles, it is oxidized and transforms into blue colored TMB(ox) form. When S-protein (11) is added to this medium in the presence of bio-receptor (2), during the combination of bio-receptor (2) with S-protein (11), the thiol in the structure are transformed into disulfide, and TMB(ox) is reduced and is transformed into colorless TMB form. By means of this, colorimetric biosensors have been developed which are compliant to POC nature for the viruses in corona-virus (1) family.

The biosensor where colorimetric method is used as transducer can be obtained by means of pluralities of embodiments. The colorimetric biosensor can be considered not only in eppendorf tubes but also on paper. Here, as analyte is added to the structure including the oxidizing blue colored reagent solution and the bio-receptor (2) which exists on this paper, the patient shall be able to easily understand that he/she has corona-virus (1) or not by means of qualitative observation.

Figure 4:
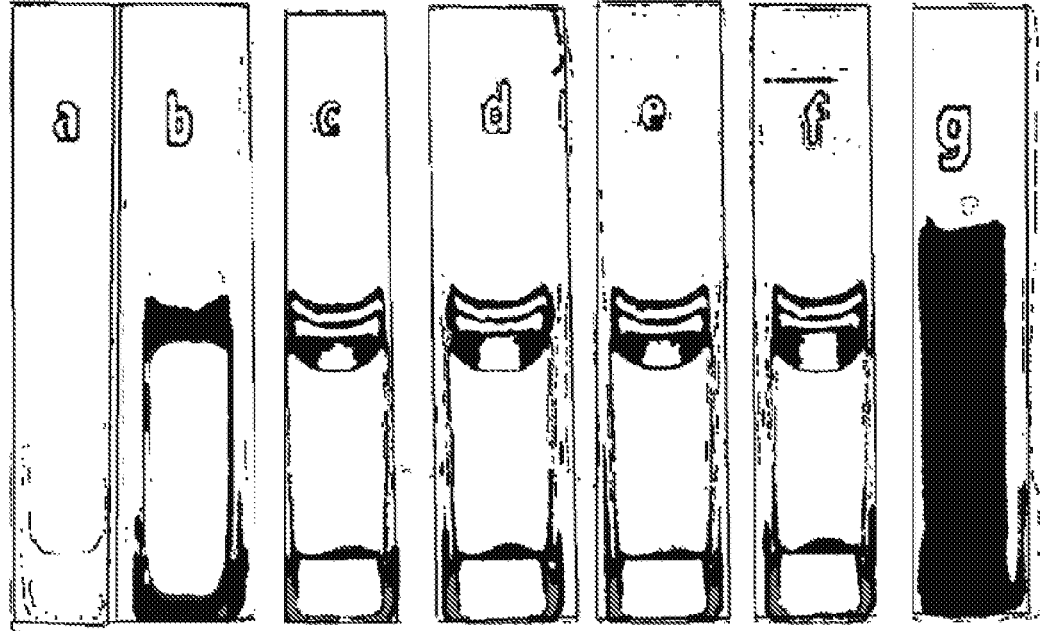
In FIG. 4, the view of steps of preparing colorimetric biosensor and of disappearance of blue color after interaction between the analyte and the biosensor is given.

In FIG. 4, the usage of colorimetric method as transducer is shown. In the first tube shown as (a), TMB solution comprising H2O2 is provided. In tube (b), Fe2O3 magnetic nano-particles are provided. Tubes (a) and (b) are stirred and tube (c) is obtained. In tube (d), TMB+Fe2O3+bio-receptor (2) exist. In tube (e), TMB+Fe2O3+bio-receptor (2)+buffer solution exist. In tube (f), TMB+Fe2O3+S protein (11) exist. In tube (g), TMB+Fe2O3+S protein (11)+bio-receptor (2) exist. Accordingly, tube (a) is colorless and tube (b) is black. Tubes (c), (d), (e) and (f) are blue. In tube (g), decolorization has been observed as desired. Thanks to this, as also seen in tube (g), the qualitative analysis of the interaction of the subject matter bio-receptor (2)+S protein (11) becomes possible.

As seen, the biosensor obtained in the invention can be embodied according to the transducer which is to be used. Within this context, bio-receptor (2)-corona-virus (1) interaction and the measurement of the obtained biological event are forming the base of the invention. For this reason, each equipment or component, which optimizes measurement of said biological event, can be added to the biosensor. As example to these, electronic signal amplifiers, data processing devices and additional auxiliary transducers can be given. For instance, if the electrochemical biosensor can be combined with a miniaturized potentiostat, a system which is compliant to POC nature can be obtained.

Thanks to the particularly colorimetric biosensor obtained in the invention, the patient can test himself/herself easily. Thanks to this, population in hospitals resulting from tests can be reduced. Moreover, the patient can quarantine himself/herself rapidly for stopping infecting speed.

Thanks to the biosensor obtained in the invention, the cost of tests will reduce. Moreover, the need for a specialist for the test is eliminated. As the cost of the test is reduced, a more reachable test result can be obtained. Besides, the developed bio-sensors are suitable for realizing diagnosis of viruses like influenza by being based on infection steps by changing the required reagents.

What is claimed is:

1. A method for determining a presence of a corona-virus, comprising: qualitatively or quantitatively measuring the presence of the corona-virus in an analyte by an electrochemical transducer method by a biosensor including an ACE2 bio-receptor for a SARS virus and a SARS-2 virus, a DPP4 bio-receptor for a MERS virus, and a CD147 bio-receptor for the SARS-2 virus in a corona-virus family, wherein the method comprises the following process steps:

contacting the analyte, taken from a person in need, with the bio-receptors immobilized onto a working electrode, conducting an interaction between the bio-receptors and S-proteins of the corona-virus existing in the analyte, differentiating an impedance on a surface of the working electrode by binding of the S-proteins to the bio-receptors and determining whether the person in need is infected with a corona-virus by measuring a change.

2. The method according to claim 1, wherein gold and carbon based electrodes are used as the working electrode.

3. The method according to claim 1, wherein an immobilization process of the bio-receptors onto the surface of the working electrode takes place by an EDC/NHS cross-binder chemical compounds.

4. A method for determining a presence of a corona-virus, comprising: quantitatively measuring the presence of the corona-virus in an analyte by a colorimetric transducer method by a biosensor including an ACE2 bio-receptor for a SARS virus and a SARS-2 virus, a DPP-4 bio-receptor for a MERS virus, and a CD147 bio-receptor for the SARS-2 virus in a corona-virus family, wherein the method comprises the following process steps: firstly adding a color forming and oxidizing reagent solution into an eppendorf tube to obtain a resulting tube, and afterwards adding a proper amount of the bio-receptors in the resulting tube to obtain a blue reacted bio-receptor solution, adding the analyte obtained from a person in need into the blue reacted bio-receptor solution for mixing to lose a blue color as a result, wherein decolorization of the solution indicates the presence of corona-virus in the analyte; wherein $\gamma$-$Fe_2O_3$ magnetic nanoparticles and a 3,3',5,5'-tetramethylbenzidine (TMB) solution containing $H_2O_2$ are used as the color forming and oxidizing reagent solution.

5. The method according to claim 4, wherein a binding region of a S-protein provided in a body of the corona-virus is bonded to the bio-receptors provided on a healthy cell surface, the blue reacted bio-receptor solution containing the $H_2O_2$ oxidizes a thiol in a structure of a bio-receptor bound to the S-protein to a disulfide bond, and the blue reacted bio-receptor solution is reduced to lose the blue color.

6. The method according to claim 1, wherein the analyte is obtained by swabbing from a mouth and a nose of the person in need.

7. The method according to claim 2, wherein the analyte is obtained by swabbing from a mouth and a nose of the person in need.

8. The method according to claim 3, wherein the analyte is obtained by swabbing from a mouth and a nose of the person in need.

9. The method according to claim 4, wherein the analyte is obtained by swabbing from a mouth and a nose of the person in need.

10. The method according to claim 5, wherein the analyte is obtained by swabbing from a mouth and a nose of the person in need.

* * * * *